United States Patent [19]
Pero

[11] Patent Number: 5,925,571
[45] Date of Patent: Jul. 20, 1999

[54] METHOD OF TESTING IMMUNE COMPETENCY

[75] Inventor: Ronald W. Pero, Lund, Sweden

[73] Assignee: Oxi-Gene, Inc., Boston, Mass.

[21] Appl. No.: 08/847,664

[22] Filed: Apr. 22, 1997

Related U.S. Application Data

[63] Continuation of application No. 08/330,015, Oct. 27, 1994, abandoned.
[51] Int. Cl.$^6$ .......................... G01N 33/48; G01N 33/49; G01N 33/50
[52] U.S. Cl. .............................. 436/120; 436/64; 436/86; 436/119; 436/164; 435/974
[58] Field of Search ................................... 436/119, 120, 436/86, 64, 164; 435/974

[56] References Cited

FOREIGN PATENT DOCUMENTS 0229674  7/1987  European Pat. Off. .

OTHER PUBLICATIONS

Ammon et al., Diabetologia 32:797–800, 1989.
Ayers et al., Anal. Biochem. 154:186–93, 1986.
Banford et al., Rheumatol. Int. 2:107–11, 1982.
Baruchel and Wainberg, J. Leuk. Biol.. 52:111–14, 1992.
Belch et al., Br. Heart J. 65:245–48, 1991.
Belch et al., Free Radic. Biol. Med. 6:3375–78, 1989.
Berger, Methods Cel Biol. 20:325–340, 1988.
Beutler and Gelbert, J. Lab. Clin. Med. 105:581–04, 1985.
Buhl et al., The Lancet, 1294–98, Dec. 2, 1989.
Bergunder et al., Eur. J. Clin. Invest. 18:420–24, 1988.
Burgunder and Lauterburg, Eeur. J. Clin. Invest. 17:408–14, 1987.
Carson et al., J. Exp. Med. 163:746–51, 1986.
Cerutti, Science 227:375–81, 1985.
Cross et al., Ann. Int. Med. 107:526–45, 1987.
Droege et al., Immunobiology 172:151–56, 1986.
Eck et al., Biol. Chem. Hoppe Seyler 370:101–81, 1989.
Edgren et a., Int. J. Rad. Biol. 40:355–63, 1985.
Edgren and Revesz, Int. J. Rad. Biol. 48:207–12, 1985.
Ellman, Arch. Biochem. Biophys. 82:70–77, 1959.
Evans, Curr. Med. Res. Opin. 3[5]: 268–73, 1975.
Evans, Proc. Roy. Soc. Med. 70:95–97, Supp. 3, 1987.
Fidelius et al., Exp. Cell Res. 170:269–75, 1987.
Fidelius and Tsan, Immunology 61:503–08, 1987.
Fischman et al., J. Immunol. 127: 2257–62, 1981.
Hall et al., Ann. Rheum. Dis. 40:194–97, 1981.
Hall and Gillan, J. Pharm. Pharmacol. 31:676–80, 1979.
Hamilos and Wedner, J. Immunol. 135:2740–47, 1985.
Harmon, Age 7:111–31, 1984.
Ikai et al., Proc. Natl. Acad. Sci. USA 77:3682–85, 1980.
Imai, Methods in Enzymology 143:6775, 1987.
Jocelyn, Methods in Enzymology 143:44–67, 1987.
Johnson et al., Int. J. Biochem. 22:67–73, 1990.
Johnstone and Williams, Nature 300:368–79, 1982.
Kosower, Int. Rev. Cytol. 54:109–60, 1978.
Lunec et al., J. Rheumatol. 8[2]:233–45, 1981.
MacDermott et al., Immunology 57:521–26, 1986.
Marnett, Carcinogenesis 8:1345–73, 1987.
Martensson, Metabolism 35:118–21, 1986.
Mazen et al., Nucleic Acids Res. 17:4689–98, 1989.
Meister, Science 220:472, 1983.
Mimic–Oka et al., Biochem. Med. Met. Biol. 39:48–54, 1988.
Nathan, J. Clin. Invest. 80:1550–60, 1987.
Pero et al., Carcinogenesis 6:1055–58, 1985.
Pero et al., Mutation Res. 142:69–73, 1985.
Pero et al., Carcinogenesis 10:693–97, 1989.
Pero et al., Carcinogenesis 10:1657–64, 1989.
Pero et al., Cancer Det. Prevent. 14:555–61, 1990.
Pero et al., Cancer Res. 50:4619–25, 1990.
Pero et al., J. Neurosurg. 77:601–06, 1992.
Pullar et al., Br. J. Rheumat. 26:202–06, 1987.
Rae et al., Ann. Rheum. Dis. 45:839–46, 1986.
Satoh and Lindahl, Nature 356: 356–58, 1992.
Schraufstratter et al., J. Clin. Invest. 85:554–62, 1990.
Scovassi et al., Carcinogenesis 8:1295–1300, 1987.
Singh et al., Anal. Biochem. 213:49–56, 1993.
Spitz et al., J. Cell Physiol. 156:72–9, 1993.
Sstacey and Craig, Experienta 45:180–81, 1989.
Valis, The Lancet 337:918–919, 1991.
Van Rensberg et al., Free Radic. Biol. Med. 11:285–91, 1991.
Vendemiale et al., J. Hepatology 9:359–65, 1989.
Weiss et al., J. Clin. Invest. 70:598–697, 1982.
Wilson et al., Diabetologia 27:587–91, 1984.
DiSimplicio et al., (1991) Free Rad. Res. Comm. vol. 14 pp. 253–262.
Pryor et al., (1991) Free Rad. Biol. Med. vol. 10, pp. 177–184.
Chemical Abstracts CA:122:236410 Fauvier, A.E., Trace Elem. Free Radicals Oxid. Dis., [Proc. Int. Congr. Trace Elem. Med. Biol.] 4th (1994), 57–80. Eds: Fauvier, AE: Neve, J.; Faure, P. Pu61: AOCS, Champaign, Ill.

*Primary Examiner*—Jan Ludlow
*Attorney, Agent, or Firm*—Cooper & Dunham LLP

[57] ABSTRACT

A method of testing the immune competency of an individual by determining, from a sample of the blood of the individual, a value for total plasma/serum thiols including both protein thiols and nonprotein thiols, and comparing the value so determined with a reference value of total plasma/serum thiols to ascertain whether the determined value is higher or lower than the reference value, a determined value lower than the reference value being indicative of impaired immune function.

5 Claims, 5 Drawing Sheets

METHOD OF TESTING IMMUNE COMPETENCY

This is a Continuation of application Ser. No. 330,015, filed Oct. 27, 1994, now abandoned.

BACKGROUND OF THE INVENTION

This invention relates to methods of testing human individuals for impaired immune function indicative of the presence of, or predisposition to, diseases associated with compromised immune competency. Such tests may be used, for example, diagnostically, prognostically, and as a guide in determining the need for preventive or therapeutic treatment for the disease or condition so indicated.

More particularly, the invention employs a surrogate measure of DNA repair activity based on serum/plasma thiol status as a biomarker of human health. Thus, the method of the invention involves the measurement of chemically reactive thiols present in naturally occurring amino acids, polypeptides and proteins found in human serum or plasma. The concentration of these thiols can predict DNA repair capacity and immune cell responsiveness, and they are therefore useful indicators of disease progression where impaired immune function is an essential component of the disease. HIV infection, AIDS, cancer and autoimmune disorders are examples of diseases that have immunological components.

European patent No. 0 229 674 as well as several recently published papers (Pero et al, Carcinogenesis 6:1055–58, 1985; Pero et al, Mutation Res. 142:69–73, 1985; Pero et al, Carcinogenesis 10:693–97, 1989; Pero et al, Carcinogenesis 10:1657–64, 1989) disclose that DNA repair in general, and specifically the quantitative estimation of adenosine diphosphate ribosyl transferase (ADPRT), is a useful endpoint to estimate health risks in the detection, prevention and treatment of human chronic age-associated diseases such as cancer, conditions that predispose to cancer, and autoimmune diseases. In another aspect, cellular ADPRT activity has been shown to relate to immune cell responsiveness (Scouvassi et al, Carcinogenesis 8:1295–1300, 1987; Pero et al, J. Neurosurg. 77:601–06, 1992; Johnstone and Williams, Nature 300:368–79, 1982; Johnson et al, Int. J. Biochem. 22:67–73, 1990), and both these parameters have been shown to be modulated by the cellular reduction/oxidation (redox) balance thought to be in turn mediated by the thiol containing peptide, glutathione (Pero et al, Cancer Det. Prevent. 14:555–61, 1990; Pero et al, Cancer Res. 50:4619–25, 1990; Fidelius et al, Exp. Cell Res. 170:269–75, 1987; Fidelius and Tsan, Immunology 61:503–08, 1987; Fischman et al, J. Immunol. 127:2257–62, 1981; Hamilos and Wedner, J. Immunol. 135:2740–47, 1985).

Glutathione exists in the millimolar range within cells (Kosower, Int. Rev. Cytol. 54:109–60, 1978; Meister, Science 220:472, 1983) and as such it is believed to be the primary cellular reductant protecting cells from oxidative cellular injury. However, glutathione levels in human serum/plasma (i.e. 2–27 $\mu$moles/liter in Buhl et al, The Lancet, 1294–98, Dec. 2, 1989; Ayers et al, Anal. Biochem. 154:186–93, 1986) represent only a minor portion of the total reactive thiol groups present because the proteins in serum/plasma constitute the major source of reactive thiol groups (i.e. 113–133 $\mu$moles/liter in Ellman, Arch. Biochem. Biophys. 82:70–77, 1959 and Ayers et al, Anal. Biochem. 154:186–93, 1986). Therefore, the art teaches that there are at least two distinct classes of thiols in serum/plasma and other biological tissues; namely protein thiols and nonprotein thiols. A review of the literature supports that conventional procedures for the analysis of serum/plasma thiols in relation to human health consequences are based on the analysis of nonprotein thiol sources such as glutathione or cysteine where protein thiols are excluded from the analysis by the assay procedure or removed by precipitation using agents such as trichloroacetic acid, metaphosphoric acid, sulfosalicylic acid or perchloric acid before any analysis of nonprotein thiols is undertaken (Beutler and Gelbert, J. Lab. Clin. Med. 105:581–04, 1985; Buhl et al, The Lancet, 1294–98, Dec. 2, 1989; Eck et al, Biol. Chem. Hoppe Seyler 370:101–81, 1989; Burgunder et al, Eur. J. Clin. Invest. 18:420–24, 1988; Burgunder and Lauterburg, Eur. J. Clin. Invest. 17:408–14, 1987; Mimić-Oka et al, Biochem. Med. Met. Biol. 39:48–54, 1988; Mårtensson, Metabolism 35:118–21, 1986; Vendemiale et al, J. Hepatology 9:359–65, 1989). Nonprotein thiol analysis of biological samples has evolved as the standard assay procedure principally because of the strong scientific belief that glutathione, a nonprotein thiol, is the primary cellular reductant protecting cells against the harmful health effects of oxidant injury (Meister, Science 220:472, 1983).

Oxidative cellular damage has been postulated to be an important factor in (i) ageing (Harmon, Age 7:111–31, 1984), (ii) diabetes (Wilson et al, Diabetologia 27:587–91, 1984), (iii) drug resistance (Spitz et al, J. Cell Physiol. 156:72–9, 1993), HIV+/AIDS (Baruchel and Wainberg, J. Leuk. Biol. 52:111–14, 1992), (iv) initiation and promotion of cancer (Marnett, Carcinogenesis 8:1345–73, 1987; Cerutti, Science 227:375–81, 1985), (v) etiology of cardiovascular and autoimmune diseases (Cross et al, Ann. Int. Med. 107:526–45, 1987) and (vi) modulation of immune function (Carson et al, J. Exp. Med. 163:746–51, 1986). Most of this evidence comes from evaluating oxidative stress by comparing glutathione deficient to glutathione proficient cells. For example, glutathione (or cysteine, its synthetic precursor) deficiency has been shown to (i) predispose cells to increased sensitivity to DNA damage (Edgren et al, Int. J. Rad. Biol. 40:355–63, 1985; Valis, The Lancet 337:918–19, 1991), (ii) inhibit DNA repair (Pero et al, Cancer Res. 50:4619–25, 1990; Edgren and Revesz, Int. J. Rad. Biol. 48:207–12, 1985), or (iii) induce immune cell response deficiency (Hamilos and Wedner, J. Immunol. 135:2740–47, 1985; Fischman et al, J. Immunol. 127:2257–62, 1981; MacDermott et al, Immunology 57:521–26, 1986; Droege et al, Immunobiology 172:151–56, 1986; Stacey and Craig, Experienta 45:180–81, 1989). In other words, the art teaches that the nonprotein thiol component is the important factor relating oxidative cellular damage to human disease development, and the protein thiol component, which quantitatively dominates in biological samples, has no direct or regulatory relevance to the health consequences of redox imbalance, and if it indicates anything at all, it is an indirect and nonspecific estimate compared to the major regulatory role of the nonprotein thiol component.

Additional evidence for this interpretation is taken from the medical literature where serum/plasma thiols have been employed to monitor health disorders. Malignant disease (Beutler and Gelbert, J. Lab. Clin. Med. 105:581–84, 1985), chronic renal insufficiency (Mimić-Oka et al, Biochem. Med. Met. Biol. 39:48–54, 1988), glucose mediated insulin secretion (Ammon et al, Diabetologia 32:797–800, 1989), ethanol ingestion (Burgunder et al, Eur. J. Clin. Invest. 18:420–24, 1988; Vendemiale et al, J. Hepatology 9:359–65, 1989), fasting (Mårtensson, Metabolism 35: 118–21, 1986), HIV infection (Buhl et al, The Lancet, 1294–98, Dec. 2, 1989), AIDS (Eck et al, Biol. Chem. Hoppe Seyler, 370:101–08, 1989), and cirrhosis (Burgunder and Lauterburg, Eur. J. Clin. Invest. 17:408–14, 1987) represent nearly all the medical conditions where serum/plasma thiols have been used successfully to monitor health disorders. In all cases, serum/plasma nonprotein thiols such as glutathione or cysteine were estimated, and great care was taken to eliminate protein thiols from the assay procedure. These data clearly indicate that it was not obvious to one skilled in the art to include serum/plasma protein thiols in the analyses, or that they might be indicators of the health consequences of oxidative stress, as good as, or even better than, the nonprotein thiols.

Congestive heart failure (Belch et al, Br. Heart J. 65:245–48, 1991) and rheumatoid arthritis (Pullar et al, Br. J. Rheumat. 26:202–06, 1987) are the only exceptions found in the scientific literature where both serum/plasma protein and nonprotein thiols were included in the final analyses. However, the logic behind these exceptions did not indicate that total serum/plasma protein and nonprotein thiols were a better indicator of the health consequences of oxidative cellular damage than were serum/plasma nonprotein thiols. Contrarily, it was postulated in these studies that because serum/plasma albumin was an important factor to these diseases, and because albumin is the major protein component of serum/plasma and contains numerous thiol functions, it followed that estimating total serum/plasma protein and nonprotein thiols was an effective surrogate measure of the oxidation state of albumin. Therefore, the inclusion in the serum/plasma thiol assay of nonproteins such as glutathione or cysteine and proteins other than albumin added no significant methodological advantage even though they were included in the final analyses and contaminated the estimation of albumin thiols.

SUMMARY OF THE INVENTION

The present invention broadly contemplates the provision of a method for testing the immune competency of an individual, comprising the steps of obtaining a sample of blood of an individual to be tested; determining, from the sample, a value for total plasma/serum thiols, including both protein thiols and nonprotein thiols, for the individual; and comparing the value so determined with a reference value of total plasma/serum thiols to ascertain whether the value so determined is higher or lower than the reference value, a determined value lower than the reference value identifying the individual as having impaired immune function of significance in detecting, preventing or treating health disorders.

The invention embraces the unexpected discovery that when the quantitative analysis of protein thiols is included in the serum/plasma assay procedure, there exists a highly significant relationship to the function of cellular DNA repair, estimated as ADPRT activity, in immune proficient mononuclear leucocytes. Because DNA repair, and specifically ADPRT activity, estimates cell functions in response to oxidative cellular damage that can predict risk to immune dysfunction and age associated diseases as has already been documented in publications discussed above, this discovery establishes that total (i.e. protein and nonprotein) serum/plasma thiols serve as a quantitative surrogate assay for the estimation of DNA repair, immune function and health risk in the detection, prevention and therapy of human diseases. Therefore, total serum/plasma sulfhydryl analyses have improved sensitivity and biological relevance over assay procedures estimating only serum/plasma nonprotein thiols such as glutathione.

The invention contemplates measuring the total level of serum/plasma thiol groups present in the protein and nonprotein components, and relating the thiol level to DNA repair, immune function and to the detection, prevention and treatment of human diseases such as cancer, AIDS, autoimmune and cardiovascular disorders. Although the invention in its broader aspects is not limited to specific procedures for total serum/plasma thiol determination, in illustrative embodiments of the invention total serum/plasma thiols can be conveniently determined by spectrophotometric or fluorometric procedures involving the development of chromophores after reaction with thiols using aromatic disulfides such as DTNB (5,5'-dithiobis-2-nitrobenzoic acid), organic or inorganic oxidants such as iodosobenzoic acid, diphenyl picrylphenyl hydrazine, benzfuroxan, 4,4' dimethylaminodiphenyl carbinol, quinones, trinitrobenzenesulfonic acid, nitroprusside, ferricyanide, cupric copper, permanganate, iodine, mercurials, nitrous acid, maleimides, halides, platinum salts, palladium ions, fluorobenzoxadiazole derivatives, or papain-thiol sensitive p-nitroanilide reaction (Jocelyn, Methods in Enzymology 143:44–67, 1987; Imai, Methods in Enzymology 143:6775, 1987; Ayers et al, Anal. Biochem. 154:186–93, 1986; Singh et al, Anal. Biochem. 213:49–56, 1993). Concentration of chromophoric agent, pH, incubation time of the reaction mixture, and state of denaturation of protein structure with agents such as sodium dodecyl sulfate, urea, or guanidinium chloride are well known variables affecting the quantification of thiols, and as such, they should be optimally controlled for each chromophoric agent and not serve as a basis to limit the scope of this invention.

In another aspect, this invention proposes to relate ADPRT activity to the serum/plasma thiol content. This is logically and theoretically accomplished by taking advantage of the facts that ADPRT is a thiol containing protein, and at least some of the thiols are located in the zinc binding domain of the enzyme which in turn controls its participation in DNA repair (Mazen et al, Nucleic Acids Res. 17:4689–98, 1989).

Therefore, ADPRT activity is dramatically up and down regulated by cellular reduction/oxidation balance which in turn is regulated and monitored by thiol status (Pero et al, Cancer Res. 50:4619–25, 1990). Furthermore, it is found that there is a natural production of ADPRT inhibitors via normal metabolic cellular processes which can inhibit DNA repair and immune cell function. These substances were identified as HOCl and N-chloramines which are well known oxidants of thiol (Schraufstatter et al, J. Clin. Invest. 85:554–62, 1990). It is also found that most of the total serum/plasma thiols are chemically reactive with N-chloramines, and as such, this parameter can be used as a surrogate indicator of the endogenous cellular production of HOCl/N-chloramines. Because HOCl/N-chloramines produced as byproducts of cellular metabolism also inhibit DNA repair (Van Rensberg et al., Free Radic. Biol. Med. 11:285–91, 1991) and immune function, the serum/plasma thiols reacting with HOCl/N-chloramines likewise measure the functional health consequences of oxidatively stressed cells that can occur in human disorders such as ageing, autoimmunity, cancer, cardiovascular disease, diabetes, drug resistance and HIV infection.

There are well known distinct classes of ADPRT activity; namely, constitutive, induced and activated ADPRT activities. DNA damage is a necessary cofactor that drives the ADPRT enzymatic activity (Satoh and Lindahl, Nature 356:356–58, 1992). The constitutive ADPRT level reflects the intrinsic or steady state enzymatic activity in response to endogenous cellular levels of DNA damage induction.

However, the ADPRT activity can be activated by exogenously supplied DNA damaging agents, such as oxidatively stressing cells by exposure to reactive oxygen species produced by phagocytes or chemical agents (Pero et al, Cancer Det. Prevent. 14:555–61, 1990), to maximum levels of ADPRT activity. Consequently, induced ADPRT activity (e.g. in response to oxidative stress) can be calculated by subtracting the constitutive ADPRT activity from the activated ADPRT activity. This invention also embraces the discovery that when ADPRT activity is activated by DNA damage and measured as either activated or induced ADPRT levels, the plasma thiol levels significantly estimate mononuclear leucocyte ADPRT enzymatic activity when determined in parallel on the same blood samples as are used to obtain the plasma samples.

Further features and advantages of the invention will be apparent from the detailed description hereinafter set forth, together with the accompanying drawings.

DETAILED DESCRIPTION

The method of the invention for testing the immune competency of a human individual comprises the steps of obtaining a sample of the blood of the individual to be tested; subjecting the sample to an assay for determining a value for total (protein+nonprotein) serum/plasma thiols for the individual; and comparing the value so determined to a reference value to ascertain whether the value so determined is higher or lower than the reference value, a determined value lower than the reference value identifying the individual as having impaired immune function.

The assay typically includes initially deriving, from the obtained blood sample, a sample of serum or plasma, and determining a value for total thiols (i.e., both protein thiols and nonprotein thiols) in the serum or plasma sample by a spectrophotometric or fluorometric procedure involving the development of chromophores after reaction with thiols using a suitable chromophoric agent, as discussed above. Such procedures, in themselves well known in the art, provide a measurement or reading, e.g. in absorbance units at 412 nm, representing a determined value of total plasma/serum thiols for the individual.

The determined value is then compared with a reference value for indicating whether the individual being tested does or does not have impaired immune function in accordance with whether the determined value of the individual's total serum/plasma thiols is below or above the reference value. That is to say, in accordance with the present invention it has now been found that, for any procedure for assaying total (protein+nonprotein) serum/plasma thiols of an individual, there exists a reference value such that a determined value for an individual's total serum/plasma thiols below that reference value identifies the individual as having impaired immune function.

Figure 5:
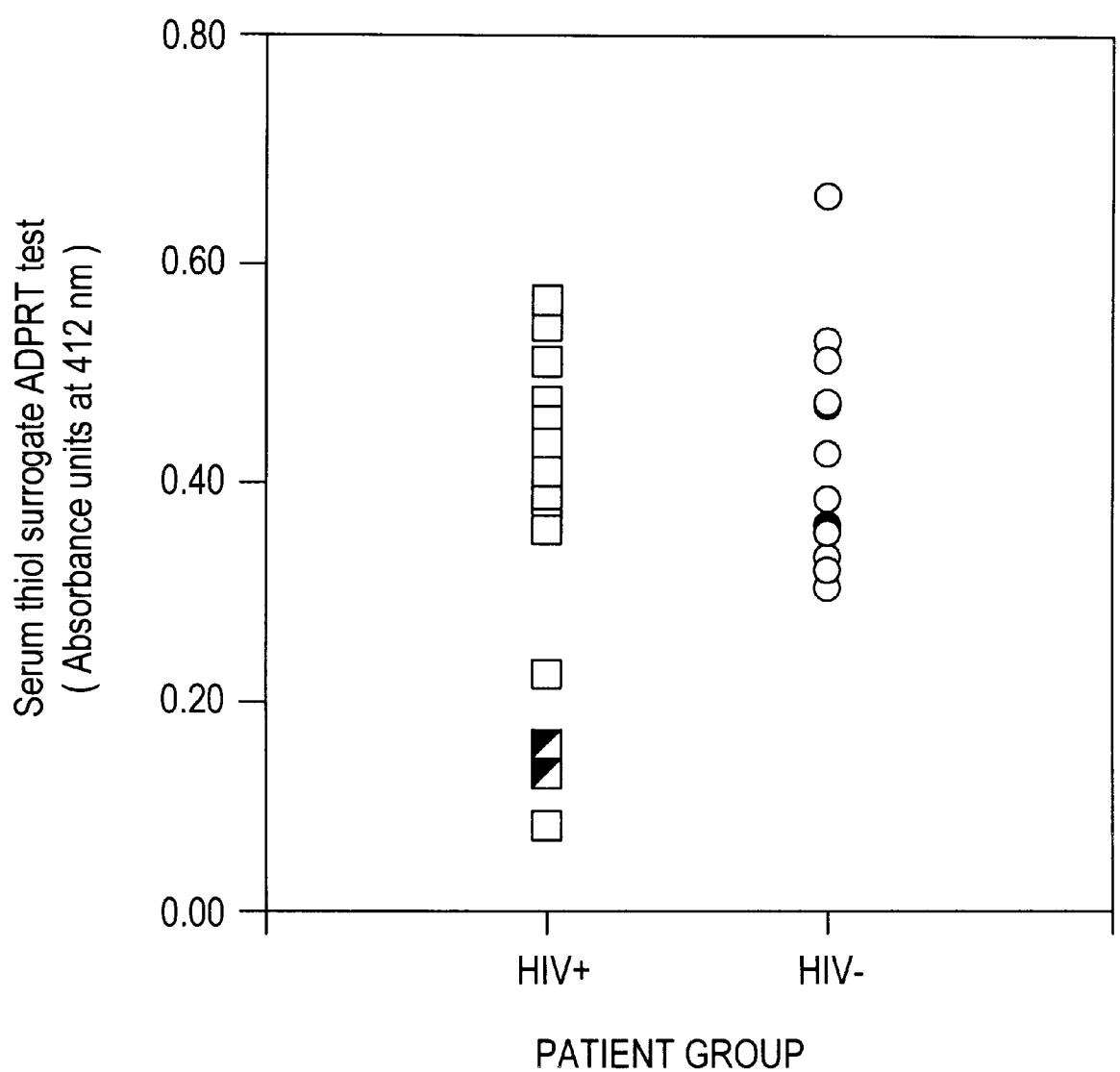
FIG. 5 is a graph illustrating a serum thiol surrogate ADPRT test for HIV positive and HIV negative patient groups.

The establishment of an appropriate reference value to function as an indicator of impaired immune function will be readily apparent to persons skilled in the art from the foregoing description. For instance, the reference value can be established by testing a number of individuals of known immune competency (impaired and unimpaired) to determine a range of values of total serum/plasma thiols of such individuals, and identifying the lower limit of the range (or selecting a point, related thereto, providing a desired confidence level of impaired or unimpaired immune function determination) as the reference value. Such a reference value is illustrated in Example 5 described below, as the lower limit of total serum thiols of an HIV− (normal immune competency) patient group. FIG. 5, representing data obtained in Example 5, shows that among HIV+ patients tested, some had determined values of total serum thiols above this reference value, and others had determined values of total serum thiols below the reference value. Within the investigatory period, fatalities occurred only in the latter (below reference value) group of HIV+ patients and not in the former (above reference value) group of HIV+ patients, substantiating the correlation between impaired immune function and determined values of total serum thiols below the reference value.

One illustrative use of the present method is as a guide to deciding whether to subject a particular patient to treatment for the condition or consequences of the impaired immune function so ascertained. For instance, in the case of HIV+ patients as represented by Example 5, those having determined values of total serum thiols below the reference value (represented by about 0.25 absorbance units at 412 nm) might be subjected immediately to such treatment while those having total serum thiol values above the reference value, indicating as-yet uncompromised immune competency, would not yet need treatment.

In a specific aspect, the method of the invention may be employed as a surrogate measure of induced ADPRT activity, which is itself an indicator of the presence of, or a predisposition to, DNA-associated diseases, as described for example in European patent No. 0 229 674.

The invention will be further described with reference to the Examples set forth below, in which the following specific procedures were employed:

Blood component preparation.—Peripheral blood samples (n=225) from apparently healthy volunteers, patients with predisposition for cancer and cancer patients were obtained by venous puncture and collected into heparinized vacutainers (143 USP units/10 ml tube). The blood samples were first centrifuged at 100×G for 10 min and the platelet rich plasma removed with a Pasteur pipette. Platelet-poor plasmas to be used in these experiments were prepared by centrifuging the platelet-rich plasmas at 400×G for 25 min to pellet the platelets. Next, the original volume of blood samples were restored by addition of physiologic saline and then they were carefully layered on top of a commercially available density cushion (1.077 gm/ml, Organon Teknika) before spinning at 400×G for 25 min. The human mononuclear leucocytes (HML) were isolated from the interphase zone of the density gradient, washed by centrifugation using RPMI 1640 medium and the cell density adjusted for in vitro culturing purposes in the conventional manner. When both HML and neutrophils were needed, the cell fractions were simultaneously isolated by layering the blood sample on top of neutrophil isolation medium (Cardinal Associates), and carrying out all steps in the density gradient isolation using Krebs-Ringer phosphate buffer with glucose (KRPG, pH=7.4) according to the procedure of Nathan (J. Clin. Invest. 80:1550–60, 1987).

Cytotoxicity.—Regardless of the isolation method used for blood cell fractionation, HML were always resuspended in 10–20% serum or plasma supplemented RPMI 1640 medium, pelleted and then resuspended again in either physiologic saline or KRPG buffer for treatment with either HOCl or chloramine T (Sigma). HOCl concentration was determined from the $e_{235}$=100 $M^{-1}$ $cm^{-1}$. Cytotoxicity was monitored by cellular exclusion of trypan blue (0.2% isotonic solution+5% serum) after 15 min incubation with the dye at 37° C. The cytotoxicity of HOCl and N-chloramines is well known (Schraufstatter et al, J. Clin. Invest. 85:554–62, 1990). Hence, it was important to determine that any biochemical effects on ADPRT activity induced by these agents were not related to acute cytotoxicity. The experimental conditions outlined above, and used to collect the data reported on herein, were non-acutely cytotoxic.

HOCl measurement.—Mixed cultures of HML+ neutrophils were assayed for the production of HOCl in the extracellular conditioned medium by removal of the cells by centrifugation following the incubation period, and immediately trapping the produced HOCl with taurine (20 mM). Taurine chloramine was then quantified spectrophotometrically by using the conversion of $I^-$ to $I_2$ ($E=2.29\times10^4$ $M^{-1}$ $cm^{-1}$). Details of this procedure have been described by Weiss et al (J. Clin. Invest. 70:598–607, 1982).

ADPRT assay.—The procedure was adapted from the permeabilized cell technique of Berger (Methods Cell Biol. 20:325–340, 1988) with modifications as previously described (Pero et al, Carcinogenesis 10:1657–64, 1989). Duplicate samples of $1\times10^6$ HML in the presence of 0 to $4\times10^6$ neutrophils were cultured in 1 ml of KRPG buffer for 30 min at 37° C. in the presence of PMA (phorbol-12-myristate-13-acetate, 25 ng/ml). After this co-incubation, the HML+ neutrophil mixtures were harvested by centrifugation, permeabilized, and ADPRT activity determined by radiometric procedure as described in detail elsewhere (Pero et al, Carcinogenesis 10:1657–64, 1989). In other experiments, duplicate HML samples of $1\times10^6$ per ml KRPG buffer were directly treated with 0–100 $\mu$M dose ranges of HOCl or chloramine T for 30 min at 37° C. which was then followed immediately by treatment with a standardized dose of PMA (25 ng/ml) for another 30 min before analysis of ADPRT activity as already referred to above.

Plasma/serum thiol determination.—Plasma samples were collected from the same heparinized blood samples that were used to determine mononuclear leucocyte poly ADPRT activity. The samples were stored under liquid nitrogen until subjected to analysis. Each plasma sample was thawed and centrifuged at 2000×G to sediment any precipitated fibrin. Two ml 20% plasma in water (i.e. 4:1 dilution of plasma with water) was prepared and 30 $\mu$l of 5,5' dithiobis-(2-nitrobenzoic acid) (DTNB) was added as a 9.5 mg/ml solution dissolved in 0.1 M $K_2HPO_4$, 17.5 mM EDTA, pH 7.5. The mixture was left to react at room temperature for 1 hr, at which time the absorbance units at 412 nm ($A_{412}$) was measured. Chloramine T (Sigma) dissolved in water was then added at a final concentration of 40 $\mu$M and the $A_{412}$ again read after 30 min. Total plasma thiols as well as N-chloramine sensitive and insensitive plasma thiols were calculated by subtraction of reagent blank values from the values of total DTNB reactive and N-chloramine reactive thiols. In the study involving HIV+ (n=15) and HIV– (n=13) patients initiated in May, 1993, the same procedure was used except serum samples were analyzed instead of plasma samples. The serum samples were donated by intravenous drug users attending the Aaron Diamond Research Center for AIDS. The sera were prepared over a period of years and biologically banked at –80° until used in this study.

EXAMPLE 1

Figure 1:
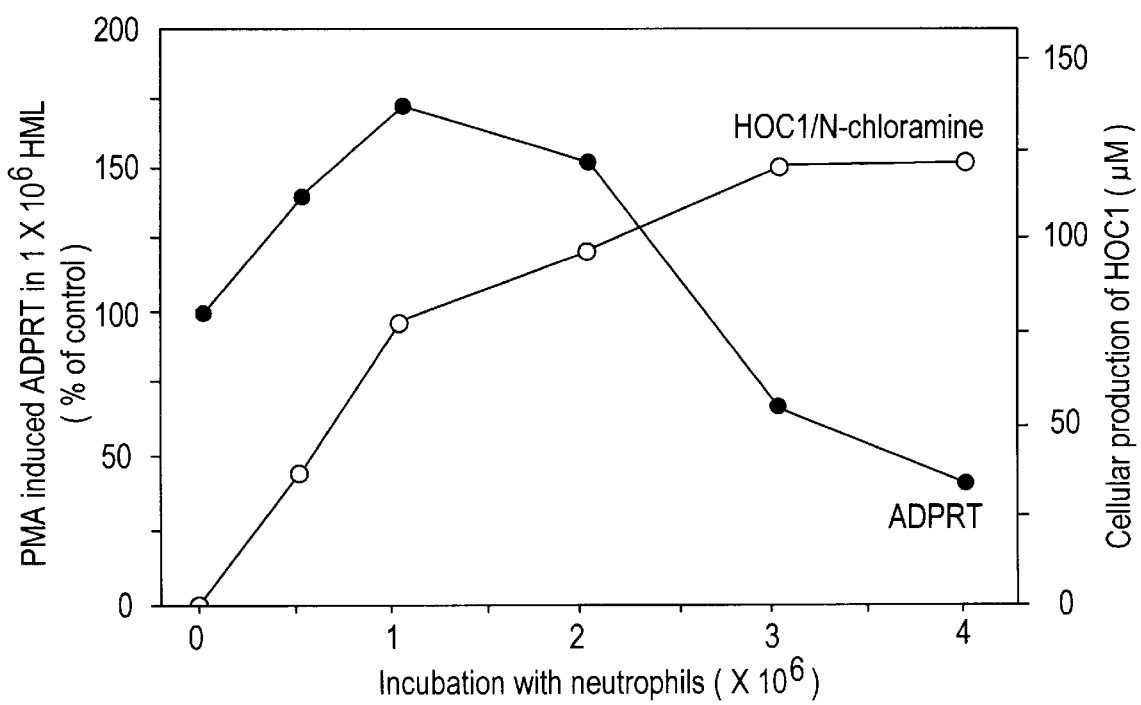
FIG. 1 is a graph in which PMA induced ADPRT in $1 \times 10^6$ HML and cellular production of HOCl are plotted against incubation with neutrophils.

This Example establishes that human phagocytes (i.e. neutrophils) produce physiologic relevant concentrations of endogenous ADPRT inhibitors. Under conditions that permit viable cell culturing, a standardized amount of HML (human mononuclear leucocytes, $1\times10^6$) was incubated together with increasing amounts of neutrophils from 0 to $4\times10^6$ cells per culture. Neutrophils do not respond to the induction of DNA damage by an activation of ADP-ribosylation, and so these cells do not contribute to the estimation of ADP-ribosylation in this experiment (Ikai et al, Proc. Natl. Acad. Sci. USA 77:3682–85, 1980). Next these combined cultures were exposed to PMA (phorbol-12-myristate-13-acetate) to activate ADP-ribosylation in HML, and to induce the production of reactive oxygen intermediates by neutrophils. The abundant reactive oxygen intermediates, hydroxyl radical, super oxide anion, and hydrogen peroxide, are all well known inducers of ADP-ribosylation (Pero et al, Cancer Det. Prevent. 14:555–61, 1990). The data in FIG. 1 show that when HML+ neutrophil ratios reached 1:2 ($\times10^6$ cells/ml), which is comparable to the proportion and concentration in blood, HML ADP-ribosylation began to become severely inhibited. The respiratory burst induced by PMA exposure of neutrophils was monitored by HOCl production. It was concluded that either the presence of neutrophils or the production of about 80 $\mu$M HOCl or N-chloramine was sufficient to cause inhibition of HML ADP-ribosylation.

EXAMPLE 2

Figure 2B:
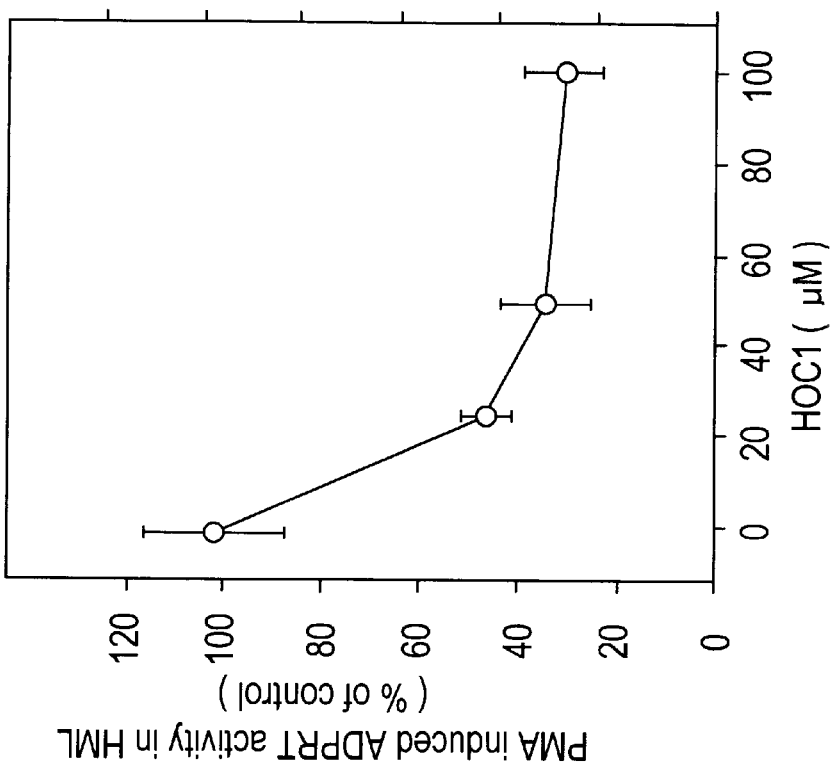
FIG. 2 is a graph having two portions in which PMA induced ADPRT activity in HML is plotted against $\mu M$ of Chloramine T and of HOCl, respectively.
Figure 2A:
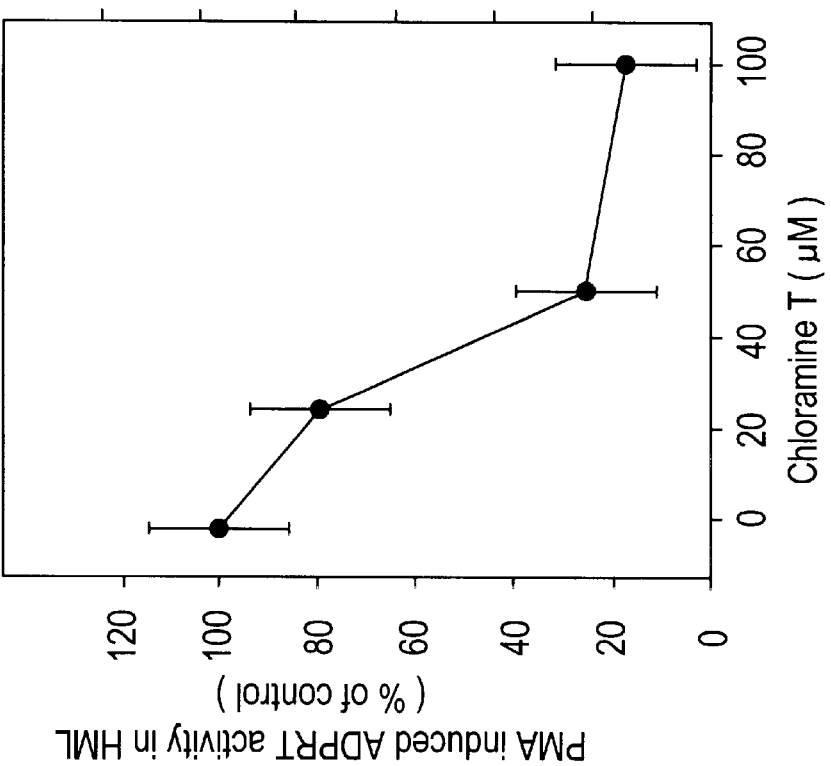

The effect of various dosage levels of chloramine T and HOCl on PMA induced ADPRT activity in HML was investigated utilizing the procedures described above for such tests, measuring the PMA induced ADPRT activity for HML subjected to the various dosages, and comparing the values obtained with measured control values of PMA induced ADPRT activity in HML from the same source but with zero dosages of chloramine T and HOCl. The results, represented in FIG. 2, confirm that HOCl and N-chloramine are potent naturally occurring ADPRT inhibitors because they can cause >80% inhibition of HML (human mononuclear leucocyte) ADPRT activity at doses of 80 $\mu$M, which are levels easily attainable in peripheral blood under culture conditions that give negligible cytotoxicity. This Example together with Example 1 clearly shows that ADPRT inhibitors are naturally produced as a by-product of the respiratory burst of phagocytes which is a normal function of this cell type designed to kill infectious agents.

EXAMPLE 3

Figure 3A:
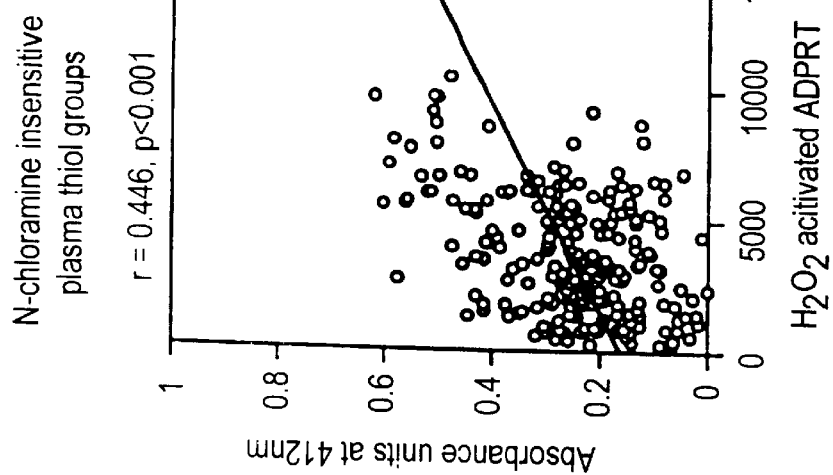
FIG. 3 is a three-part graph in which absorbance units at 412 nm are plotted against $H_2O_2$ activated ADPRT for total plasma thiol groups, N-chloramine insensitive plasma thiol groups, and N-chloramine sensitive plasma thiol groups.
Figure 3B:
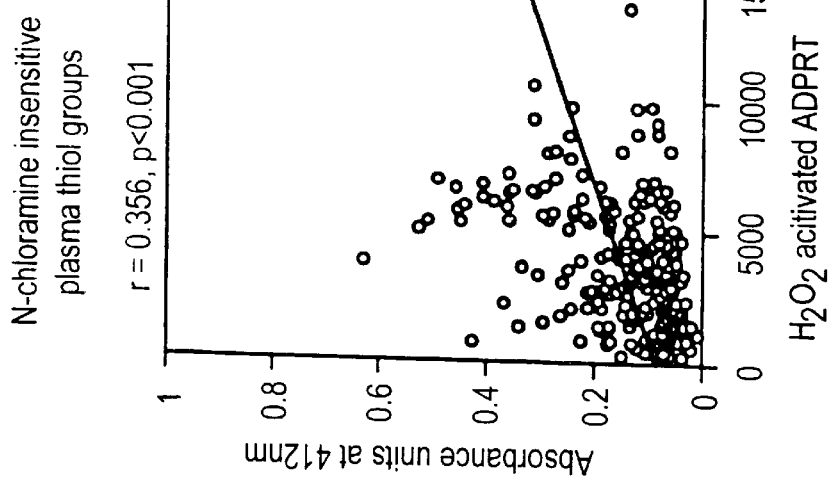
Figure 3C:
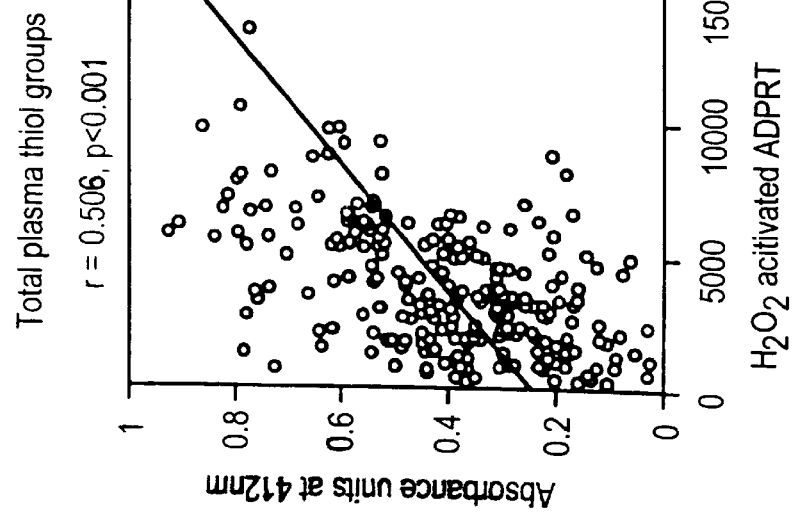

Utilizing the above-described procedures, values were determined for $H_2O_2$ activated ADPRT activity in HML and for total plasma thiols, N-chloramine insensitive plasma thiols, and N-chloramine sensitive plasma thiols coming from the same blood samples (n=225). Results are represented in FIG. 3. This Example demonstrates that plasma thiols significantly predict the level of hydrogen peroxide activated ADPRT activity determined in HML (human mononuclear leucocytes) coming from the same blood samples. Furthermore, this example shows that the N-chloramine sensitive plasma thiols give a better correlation than the N-chloramine insensitive plasma thiols to HML ADPRT activity, and that most of the N-chloramine sensitive plasma thiols are plasma protein thiols and not just nonprotein plasma thiols. Consequently, the best surrogate predictor of ADPRT activity was total protein+nonprotein plasma thiols. HOCl and N-chloramines are efficient oxidizers of thiols, and could as such in a surrogate manner indicate ADPRT activity. The logic linking ADPRT activity to plasma thiols is based on the facts (1) that ADPRT can be dose dependently up- and down- regulated by reduced and oxidized glutathione, respectively (Pero et al, Cancer Res. 50:4619–25, 1990) and (2) that ADPRT has thiol amino acid constituents in the DNA binding domain of the enzyme which in turn control its participation in DNA repair (Mazen et al, Nucleic Acid Res. 17:4689–98, 1989).

EXAMPLE 4

Figure 4A:
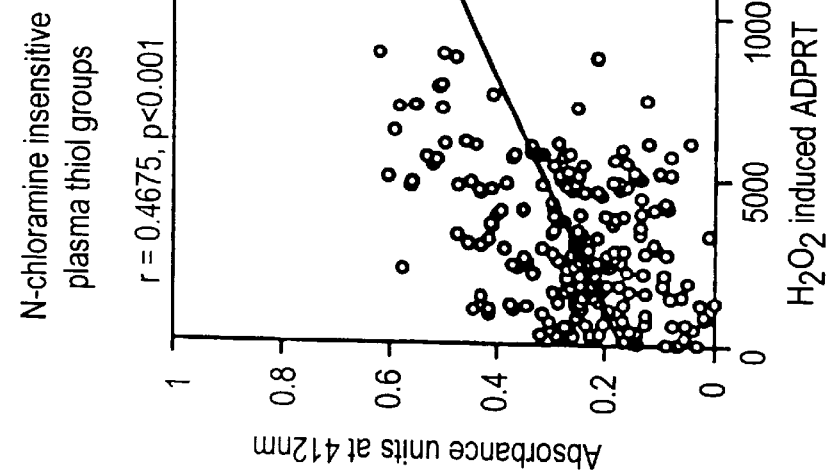
FIG. 4 is another graph similar to FIG. 3.
Figure 4B:
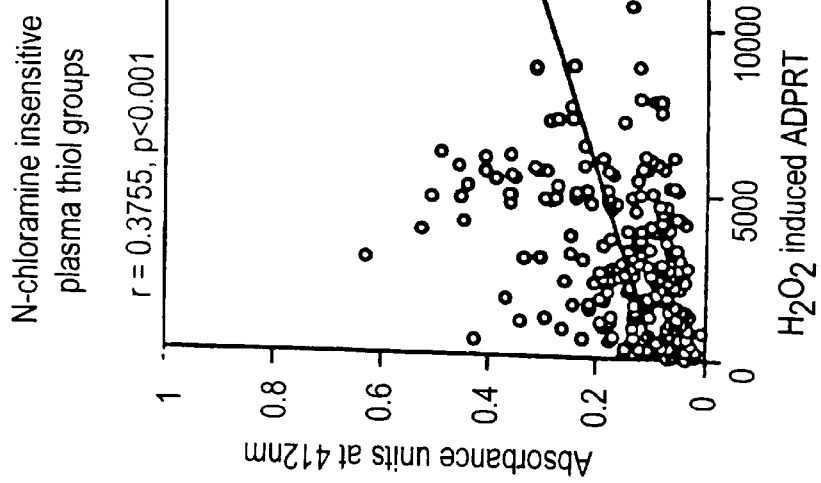
Figure 4C:
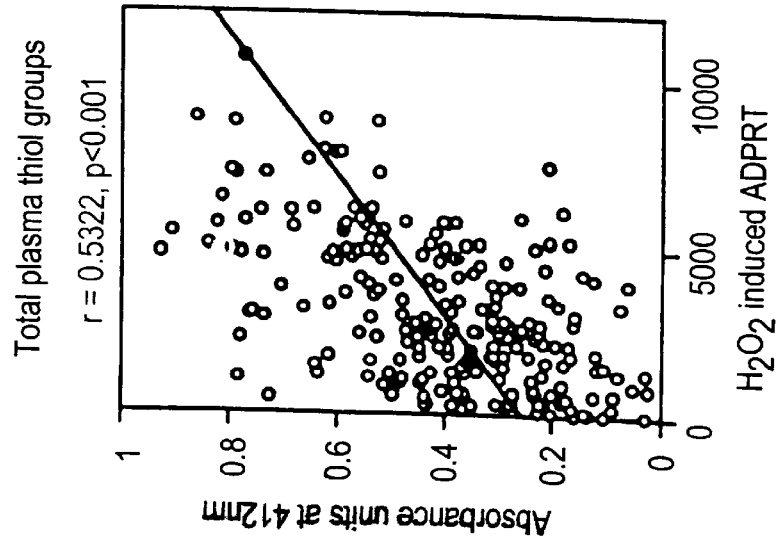

Again following the above-described procedures, tests were made to compare values of $H_2O_2$ induced ADPRT in HML with values of total plasma thiols, N-chloramine insensitive plasma thiols, and N-chloramine sensitive plasma thiols from the same blood samples. Example 4 extends the knowledge disclosed in Example 3 to show that plasma thiols can also predict hydrogen peroxide HML (human mononuclear leucocyte) induced ADPRT activity (FIG. 4). Examples 3 and 4 also teach that because the activated and induced levels of ADPRT directly relate to DNA repair in general, then plasma thiols can also be used to surrogately estimate DNA repair responses in HML.

EXAMPLE 5

The aforementioned serum samples of HIV+ and HIV− individuals were assayed by the above-described plasma/serum thiol determination procedure to determine values of total serum thiols. Results are plotted on the graph of FIG. 5.

Example 5 confirms that estimating N-chloramine sensitive serum thiols has clinical utility in that reduced levels indicate HML (human mononuclear leucocyte) ADPRT deficiency that can lead to accumulation of DNA damage and inhibition of immune function of importance in the progression of HIV+ infection to AIDS and death. The half-solid squares represent the only deaths that have occurred as of August, 1993. The study was conducted in May, 1993.

It is to be understood that the invention is not limited to the procedures and embodiments hereinabove specifically set forth, but may be carried out in other ways without departure from its spirit.

What is claimed is:

1. A method for testing the immune competency of an individual, comprising the steps of
   (a) obtaining a sample of blood of an individual to be tested,
   (b) determining by analysis, from said sample, a measured value of concentration of total plasma or serum thiols, including both protein thiols and nonprotein thiols, for said individual, and
   (c) comparing the value so determined with a reference value to ascertain whether said value so determined is higher or lower than said reference value, a determined value lower than said reference value identifying said individual as having impaired immune function of significance in detecting, preventing or treating health disorders.

2. A method according to claim 1, wherein the determining step comprises deriving, from the obtained blood sample, a sample of serum or plasma, and subjecting the serum or plasma sample to an assay for total thiols including both protein thiols and nonprotein thiols.

3. A method according to claim 2, wherein the assay comprises a spectrophotometric or fluorometric procedure involving development of chromophores after reaction with thiols using a chromophoric agent.

4. A method for testing the immune competency of an HIV+ individual, comprising the steps of
   (a) obtaining a sample of blood of an HIV+ individual to be tested,
   (b) determining by analysis, from said sample, a measured value of concentration of total plasma or serum thiols, including both protein thiols and nonprotein thiols, for said individual, and
   (c) comparing the value so determined with a reference value established by determining values for total plasma or serum thiols for HIV− individuals, to ascertain whether said value so determined is higher or lower than said reference value, a determined value lower than said reference value identifying said individual as having impaired immune function.

5. A method of testing an individual for the presence of or a predisposition to a disease associated with DNA damage, comprising
   (a) obtaining a sample of blood of an individual to be tested, and
   (b) subjecting the blood sample to a surrogate test for activated or induced activity of adenosine diphosphate ribosyl transferase (ADPRT) by the steps of
      (i) determining by analysis, from said sample, a measured value of concentration of total plasma or serum thiols, including both protein thiols and nonprotein thiols, for said individual, and
      (ii) comparing the value so determined with a reference value of total plasma or serum thiols corresponding to a reference level of ADPRT activity, to ascertain whether said value so determined is higher or lower than said reference value, wherein said presence of or predisposition to a disease associated with DNA damage is indicated if said value so determined is lower than said reference value.

* * * * *